United States Patent
Fischvogt

(10) Patent No.: US 10,813,536 B2
(45) Date of Patent: Oct. 27, 2020

(54) OPTICAL TROCAR SYSTEM

(71) Applicant: Covidien LP, Mansfield, MA (US)

(72) Inventor: Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 402 days.

(21) Appl. No.: 14/351,674

(22) PCT Filed: Oct. 16, 2012

(86) PCT No.: PCT/US2012/060392
§ 371 (c)(1),
(2) Date: Apr. 14, 2014

(87) PCT Pub. No.: WO2013/059175
PCT Pub. Date: Apr. 25, 2013

(65) Prior Publication Data
US 2014/0249371 A1    Sep. 4, 2014

Related U.S. Application Data

(60) Provisional application No. 61/548,428, filed on Oct. 18, 2011.

(51) Int. Cl.
*A61B 1/00*    (2006.01)
*A61B 17/34*   (2006.01)
(Continued)

(52) U.S. Cl.
CPC ...... *A61B 1/00154* (2013.01); *A61B 1/00096* (2013.01); *A61B 1/00131* (2013.01);
(Continued)

(58) Field of Classification Search
CPC ............ A61B 1/00089; A61B 1/00096; A61B 1/00101; A61B 1/00135; A61B 1/00142; A61B 1/00154
(Continued)

(56) References Cited

U.S. PATENT DOCUMENTS 5,674,181 A * 10/1997 Iida ...................... A61B 1/0008
                                                    600/121
5,685,823 A * 11/1997 Ito ...................... A61B 1/00091
                                                    600/121
(Continued)

FOREIGN PATENT DOCUMENTS

CA        2640388 C      12/2015
DE    202008009527 U1    10/2008
(Continued)

OTHER PUBLICATIONS

International Search Report for (PCT/US12/60392) date of completion is Mar. 21, 2013 (4 pages).
(Continued)

*Primary Examiner* — Ryan N Henderson
(74) *Attorney, Agent, or Firm* — Carter, DeLuca & Farrell LLP

(57) ABSTRACT

An optical trocar system that includes an elongated obturator member having a first diameter. The elongated obturator member has a distal region, the distal region having a first diameter section having a diameter that is substantially equal to the first diameter of the elongated obturator member. The elongated obturator member has a second diameter section having a diameter that is less than the first diameter. The optical trocar system also includes an optical member attached to the distal region of the elongated obturator member such that the optical member encapsulates the second diameter section of the elongated obturator member and at least a portion of the first diameter section. A longitudinal bore through the elongated tubular obturator member is configured to receive an endoscope.

23 Claims, 10 Drawing Sheets

(51) Int. Cl.
*A61B 1/313* (2006.01)
*A61B 17/00* (2006.01)

(52) U.S. Cl.
CPC ............ *A61B 1/313* (2013.01); *A61B 1/3132* (2013.01); *A61B 1/3137* (2013.01); *A61B 17/34* (2013.01); *A61B 17/3417* (2013.01); *A61B 17/3421* (2013.01); *A61B 17/3478* (2013.01); *A61B 2017/00526* (2013.01); *A61B 2017/00907* (2013.01); *A61B 2017/346* (2013.01); *A61B 2017/347* (2013.01); *A61B 2017/3454* (2013.01); *A61B 2017/3456* (2013.01)

(58) Field of Classification Search
USPC ........ 600/114–115, 121–125, 127, 129, 175; 604/26, 27, 43–45, 93.01, 506–510; 606/190
See application file for complete search history.

(56) References Cited

U.S. PATENT DOCUMENTS

| | | | | |
|---|---|---|---|---|
| 5,725,477 | A * | 3/1998 | Yasui | A61B 1/00091 600/121 |
| 5,817,061 | A | 10/1998 | Goodwin et al. | |
| 6,755,782 | B2 * | 6/2004 | Ogawa | A61B 1/00087 600/127 |
| 7,384,423 | B1 * | 6/2008 | Chin | A61B 17/00008 606/190 |
| 7,485,092 | B1 * | 2/2009 | Stewart | A61B 17/00008 600/104 |
| 7,938,842 | B1 * | 5/2011 | Chin | A61B 17/00008 606/190 |
| 2001/0044570 | A1 * | 11/2001 | Ouchi | A61B 1/00098 600/107 |
| 2002/0035311 | A1 * | 3/2002 | Ouchi | A61B 1/00089 600/175 |
| 2002/0183775 | A1 | 12/2002 | Tsonton et al. | |
| 2005/0033237 | A1 | 2/2005 | Fentress et al. | |
| 2005/0065543 | A1 | 3/2005 | Kahle et al. | |
| 2005/0107816 | A1 * | 5/2005 | Pingleton | A61B 17/3417 606/185 |
| 2005/0149096 | A1 * | 7/2005 | Hilal | A61M 25/0068 606/191 |
| 2005/0272975 | A1 * | 12/2005 | McWeeney | A61B 1/00071 600/113 |
| 2005/0288622 | A1 | 12/2005 | Albrecht et al. | |
| 2006/0047284 | A1 * | 3/2006 | Gresham | A61B 17/3462 606/108 |
| 2006/0224174 | A1 | 10/2006 | Smith et al. | |
| 2007/0075465 | A1 | 4/2007 | Taylor et al. | |
| 2007/0129719 | A1 * | 6/2007 | Kendale | A61B 1/00096 606/41 |
| 2007/0260121 | A1 | 11/2007 | Bakos et al. | |
| 2008/0086160 | A1 * | 4/2008 | Mastri | A61B 17/3417 606/185 |
| 2008/0262295 | A1 * | 10/2008 | Kendale | A61B 1/00096 600/104 |
| 2008/0300617 | A1 * | 12/2008 | Smith | A61B 17/3417 606/191 |
| 2009/0023986 | A1 * | 1/2009 | Stewart | A61B 17/00008 600/104 |
| 2010/0016664 | A1 | 1/2010 | Viola et al. | |
| 2010/0063450 | A1 * | 3/2010 | Smith | A61B 17/3417 604/164.01 |
| 2010/0081988 | A1 * | 4/2010 | Kahle | A61B 17/3474 604/26 |
| 2010/0318112 | A1 * | 12/2010 | Smith | A61B 17/34 606/185 |
| 2011/0313242 | A1 * | 12/2011 | Surti | A61B 1/00089 600/104 |
| 2014/0249371 | A1 | 9/2014 | Fischvogt | |

FOREIGN PATENT DOCUMENTS

| | | |
|---|---|---|
| EP | 664992 A1 | 8/1995 |
| EP | 2000099 | 12/2008 |
| JP | H08266548 A | 10/1996 |
| JP | 2005503230 A | 2/2005 |
| JP | 2006289083 A | 10/2006 |
| JP | 2007516737 A | 6/2007 |
| JP | 2008504886 A | 2/2008 |
| JP | 2008296027 A | 12/2008 |
| JP | 2011125709 A | 6/2011 |
| WO | WO 2008103400 A2 * | 8/2008 ............ A61B 17/34 |

OTHER PUBLICATIONS

Supplementary European Search Report issued in corresponding EP application No. 12840970.3 dated Jul. 8, 2015.
Examination Report issued in corresponding Australian Patent Application No. 2012326322 dated May 17, 2016.
Japanese Office Action dated Aug. 1, 2016 in corresponding Japanese Patent Application No. 2014-537147, together with English translation, 12 pages.
Examination report No. 2 in corresponding Australian Application No. 2012326322, dated Feb. 9, 2017, 4 pages.
JP Notice of Allowance dated Dec. 7, 2016 in corresponding JP Patent Application No. 2014-537147, together with English summary, 5 pages.
Australian Examination Report issued in corresponding Australian Patent Application No. 2017216514 dated Nov. 30, 2017.
Australian Examination Report issued in Australian Application No. 2017216514 dated Oct. 29, 2018.
Australian Examination Report issued in corresponding application, AU 2017216514, dated Aug. 7, 2018 (4 pages).
Canadian Office Action issued in corresponding application CA 2,852,668, dated Aug. 13, 2018 (5 pages).
First Examination Report issued in India Patent Application No. 3636/DELNP/2014, dated Feb. 25, 2020.
Brazilian Office Action issued in Application No. BR112014009508-6, dated Jan. 27, 2020.

* cited by examiner

OPTICAL TROCAR SYSTEM

CROSS REFERENCE TO RELATED APPLICATION

This application is a National Stage Application of PCT/US12/60392 under 35 USC § 371(a), filed Oct. 16, 2012, which claims the benefit of and priority to U.S. Provisional Patent Application Ser. No. 61/548,428, filed on Oct. 18, 2011, the entire contents of which are incorporated herein by reference.

TECHNICAL FIELD

The present disclosure relates to a trocar system for dissecting through body tissue. More particularly, the present disclosure relates to an optical bladeless trocar system.

BACKGROUND OF RELATED ART

Endoscopic and laparoscopic minimally invasive procedures have been used for introducing medical devices inside a patient and for viewing portions of the patient's anatomy. Typically, to view a desired anatomical site, a surgeon may insert an endoscope inside the patient to render images of the anatomical site. In endoscopic surgical procedures, surgery is performed in any hollow organ or tissue of the body through narrow endoscopic tubes (cannulas) inserted through a small entrance wound in the skin. In laparoscopic procedures, surgical operations in the abdomen are performed through small incisions (usually about 0.5 to about 1.5 cm).

SUMMARY

According to an example embodiment, the present invention may relate to an optical trocar system, comprising: an elongated obturator member having a first diameter, the elongated obturator member having a distal region, the distal region having a first diameter section having a diameter that is substantially equal to the first diameter of the elongated obturator member and having a second diameter section having a diameter that is less than the first diameter; and an optical member attached to the distal region of the elongated obturator member such that the optical member encapsulates the second diameter section of the elongated obturator member and at least a portion of the first diameter section. The optical trocar system may also comprise a cannula assembly. The elongate tubular member may be configured for insertion into the cannula assembly.

Advantageously, the optical member extends distally from the distalmost end of the tubular member. The elongate tubular member may define a longitudinal bore. The longitudinal bore may be configured to receive an endoscope. The elongated tubular member may include a housing at the proximal region, the housing including an opening and a scope retention member adjacent the opening for receiving and providing retention of an endoscope. The optical member may be at least partially transparent to permit visualization of tissue with the endoscope. The optical member may define an internal sloped surface obliquely arranged relative to a longitudinal axis. The internal sloped surface may be configured and dimensioned to be engaged by an outermost periphery of a distal end of the endoscope. The internal sloped surface may provide an air gap between the distal end of the endoscope and optical member.

The optical member may be configured to dissect between tissue planes without cutting or incising tissue. The optical member may define at its distalmost end a rounded guiding nub. A central section of an outer surface of the optical member may include a pair of diametrically opposed generally convex surfaces. The central section of the outer surface of the optical member may also include a pair of diametrically opposed generally concave surfaces that are positioned circumferentially between the pair of diametrically opposed generally convex surfaces. The optical member may be molded to the distal region of the tubular member such that an outer surface of the optical member has a diameter that is substantially the same as the outer diameter of the elongated tubular obturator member. The optical member may be hollow.

In various embodiments, the second diameter section may include at least one void, and the optical member may encapsulate at least a portion of the least one void. The optical member may be attached to the distal region of the elongated obturator member by being molded, e.g., overmolded, thereto. According to an example embodiment, the present invention may relate to an optical trocar system that includes an elongated obturator member having at its distal end an optical member, wherein a central section of an outer surface of the optical member includes a pair of diametrically opposed generally convex surfaces, and wherein the central section of the outer surface of the optical member further includes a pair of diametrically opposed generally concave surfaces that are positioned circumferentially between the pair of diametrically opposed generally convex surfaces. The optical member may be configured to dissect between tissue planes without cutting or incising tissue. The optical member may define at its distalmost end a rounded guiding nub. The elongated tubular member may include a housing at the proximal region, the housing including an opening and a scope retention member adjacent the opening for receiving and providing retention of an endoscope.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
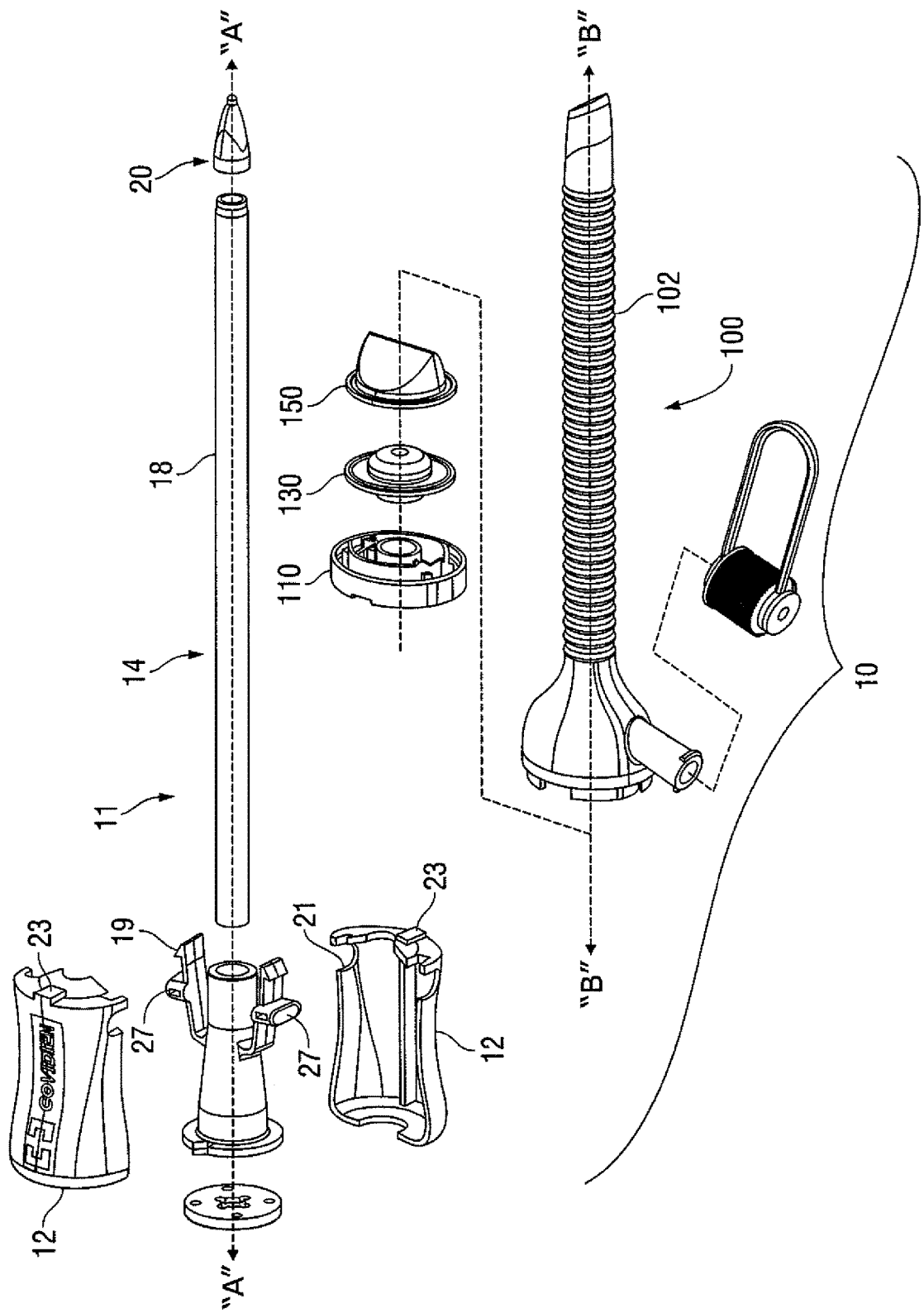
FIG. 1 is an exploded perspective of an optical trocar, e.g., visual obturator, system in accordance with an example embodiment of the present disclosure illustrating the optical access apparatus and a cannula assembly.
Figure 2:
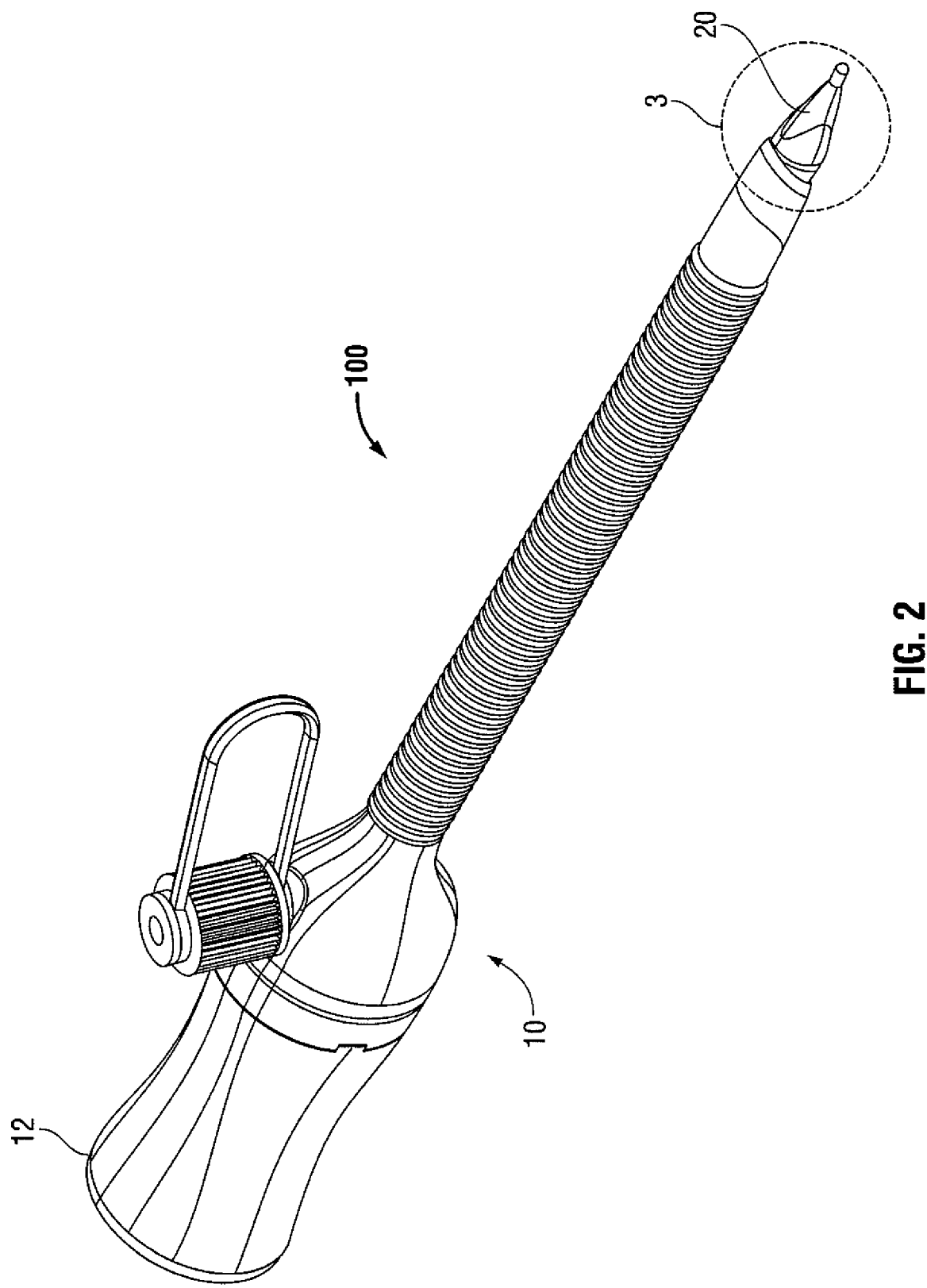
FIG. 2 is a fully assembled perspective view of the optical trocar system in accordance with the embodiment of FIG. 1.
Figure 3:
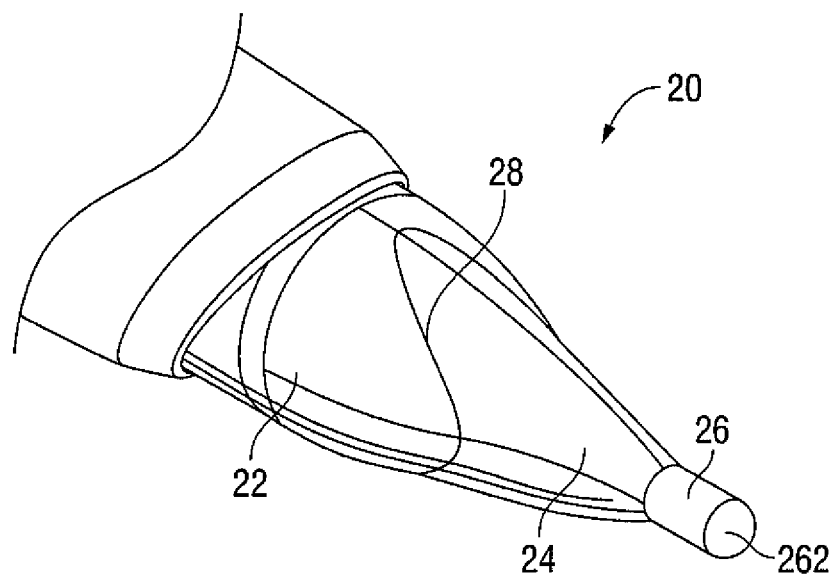
FIG. 3 is an enlarged perspective view of an optical member of the optical optical trocar in accordance with the embodiment of FIGS. 1-2.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

The present invention, in accordance with various example embodiments thereof, may relate to an optical trocar system that provides access to a body cavity through an anatomical, e.g., abdominal, wall. It should be noted that, for the purposes of this discussion, the term optical trocar system is often used herein synonymously with the term visual obturator system. Advantageously, the optical trocar system of the present invention, in accordance with various example embodiments thereof, provides such access without cutting or incising the tissue, but rather by separating tissue planes during a surgical procedure. Also, the optical trocar system of the present invention, in accordance with various example embodiments thereof, may provide visualization of body tissue fibers as they are being separated, thereby permitting a controlled traversal across a body wall, by providing a transparent optical member located at the distal end of an obturator.

Referring now to FIGS. 1 through 14, there is illustrated an optical trocar, e.g., visual obturator, system in accordance with an example embodiment of the present invention. The visual obturator is intended for separating tissue planes in an endoscopic, e.g., laparoscopic, surgical procedure, and, is particularly suitable for the blunt dissection of the abdominal lining during a surgical procedure. The visual obturator is adapted to receive an endoscope to permit viewing of tissue during the insertion and advancement of the visual obturator toward the operative site.

In accordance with the example embodiment shown, the visual obturator system 10 includes an obturator assembly 11 and a cannula assembly 100 which at least partially receives the obturator assembly 11. The obturator assembly 11 includes an obturator housing 12 disposed in mechanical cooperation with an elongated obturator member 14, and defining a longitudinal axis "A-A." The elongated obturator member 14 extends distally from the obturator housing 12.

The elongated obturator member 14 includes a rigid, e.g., metal, obturator shaft 18 attached, e.g., by over molding thereto, at its proximal end to the obturator housing 12 and at its distal end to an optical member 20. As shown in FIGS. 3-6, the optical member 20 includes a proximal section 22, a central section 24, and an atraumatic guiding nub 26. The optical member 20 has a hollow interior. As shown in FIG. 6C, a distal viewing tip of an endoscope is brought into engagement with a sloped/chamfered surface within the optical member 20, as will be described hereinbelow. Referring to FIGS. 3-6, an imaginary line 28 (shown to illustrate curvature) may delineate a boundary between the proximal section 22 and the central section 24.

Figure 4:
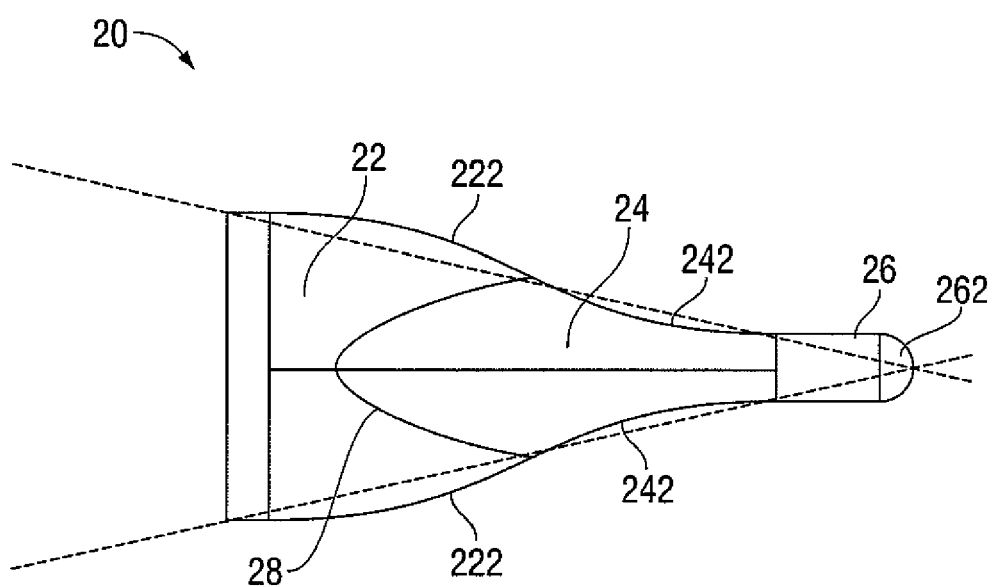
FIG. 4 is a top view of the optical member of FIG. 1.

With reference to FIG. 4, a top view of the optical member 20 is illustrated. As depicted, a proximal section 22 includes a pair of diametrically opposed convex surfaces 222. The central section 24 includes a pair of diametrically opposed concave surfaces 242. The atraumatic guiding nub 26 extending distally from the central section 24 is generally cylindrical, and includes a rounded end 262. The rounded end 262 defines a radius of curvature dimensioned to be atraumatic to tissue. Additionally, as shown in connection with phantom lines 29 that represent a cone, a portion of both the proximal section 22 and the atraumatic guiding nub 26 of optical member 20 are outside of the dimensions of the cone.

Figure 5:
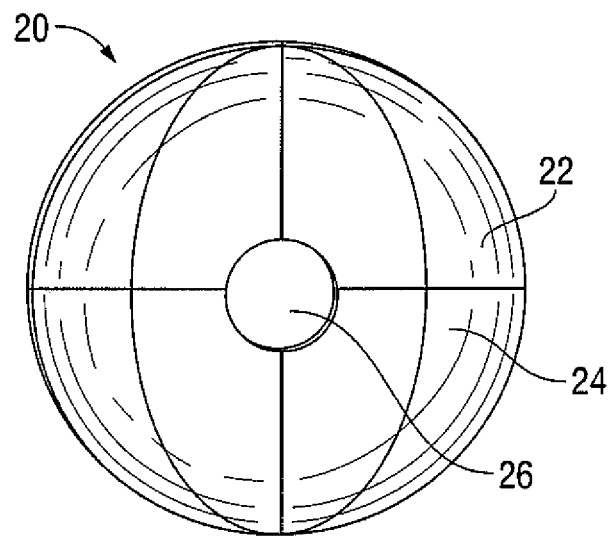
FIG. 5 is an axial view of the optical member of FIG. 3.

With reference to FIG. 5, an end or axial view of the optical member 20 illustrates the circular profile of the guiding nub 26, the oval profile of the central section 241, and the circular profile of the proximal section 22.

Figure 6:
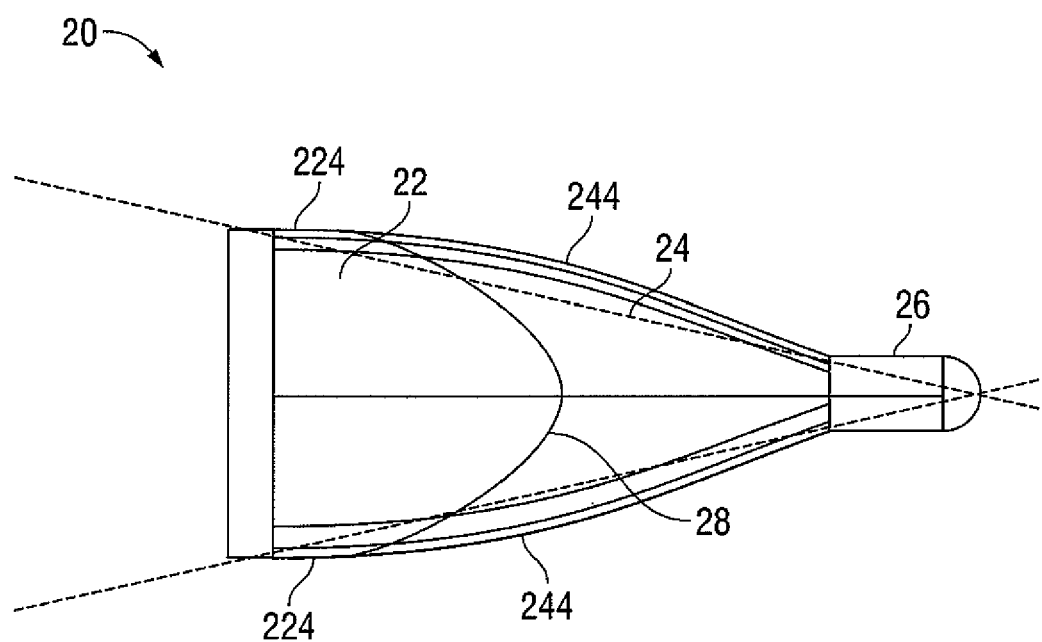
FIG. 6 is a side view of the optical member radially offset 90° relative to the top view of FIG. 4.

With reference to FIG. 6, a side view of the optical member 20 is illustrated. This side view is radially offset 90° relative to the top view of FIG. 4. As shown, the proximal section 22 of the optical member 20 further includes a pair of diametrically opposed outer surfaces 224 which are generally linear and/or convex. The central section 24 also includes a pair of opposed outer surfaces 244 which are convex. Thus, the central section 24 of the optical member 20 is inclusive of both generally concave surfaces 242 (FIG. 4) and generally convex surfaces 244 (FIG. 6) that are circumferentally spaced about the optical member 20. In this manner, the optical member 20 may have a "dolphin-nose" or "parabolic type shape. Additionally, as shown in connection with the phantom lines in FIG. 6 that represent a cone, a portion of the proximal section 22, the central section 24, and the atraumatic guiding nub 26 of optical member 20 are outside of the dimensions of the cone.

Figure 6A:
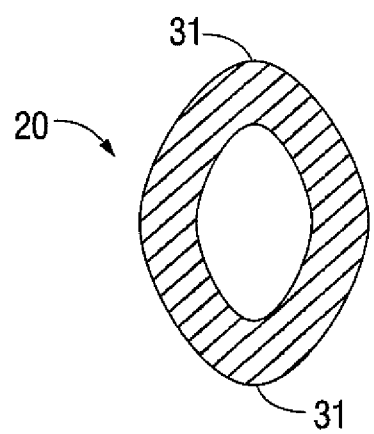
FIG. 6A is a front cross sectional view of the optical member of FIG. 6 taken at approximately the longitudinal midpoint thereof.

FIG. 6A is a front cross-sectional view of the optical member 20 taken at approximately the longitudinal midpoint thereof. The figure illustrates that the optical member 20 includes rounded outer surfaces 31 that, during use, function to help separate tissue along the tissue planes.

The atraumatic guiding nub 26 permits initial insertion within a pre-formed opening, e.g., a pre-cut scalpel incision, in the tissue and facilitates the advancement of the optical member 20 between the tissue layers to gently dissect tissue, without any cutting or incising of the tissue. After initial insertion and continued distal insertion, the central section 24 and the proximal portion 22 continue to gently enlarge the opening in tissue by further dissecting the tissue planes, e.g. by the rounded outer surfaces 31 of optical member separating the tissue planes during a clocking motion thereof.

Figure 6B:
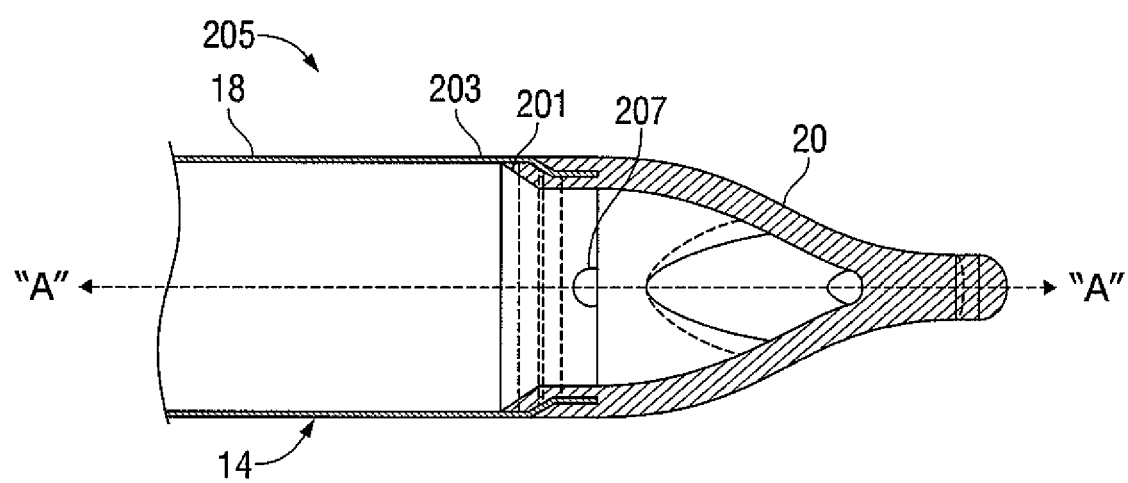
FIG. 6B is a cross sectional view of the elongated tubular member distal end region and optical member of the optical trocar system of FIG. 2.
Figure 6C:
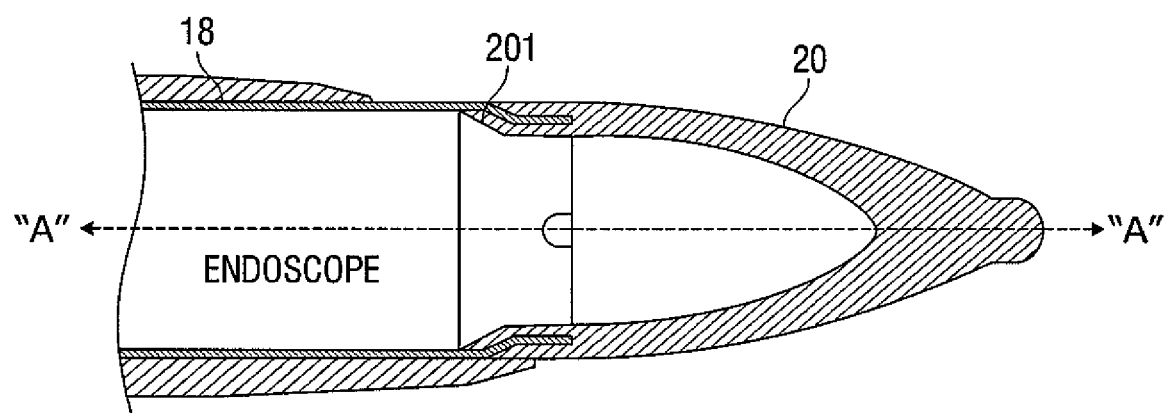
FIG. 6C is a cross sectional view of the elongated tubular member distal end region and optical member of the optical access apparatus of FIG. 6B with an endoscope positioned therein.
Figure 7:
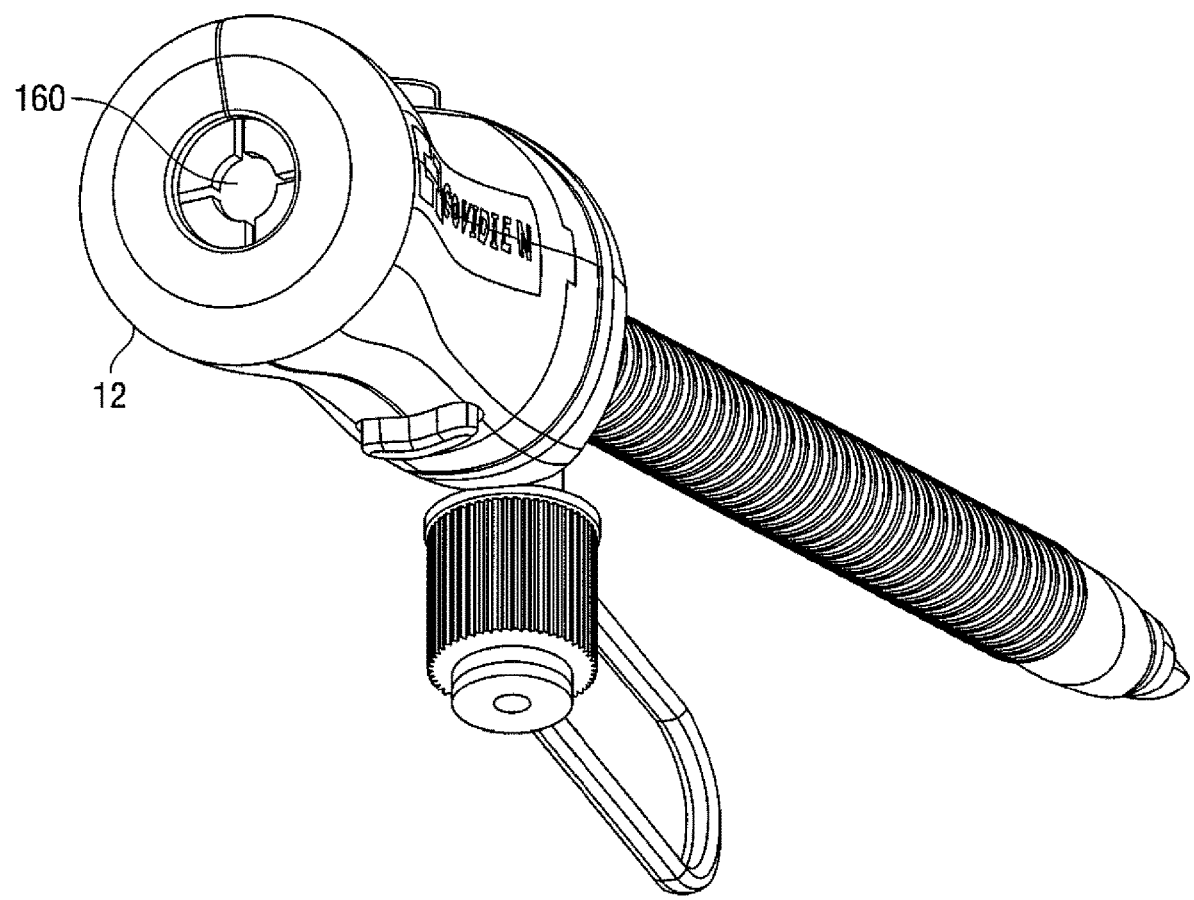
FIG. 7 is a perspective rear view of the fully assembled optical trocar system of FIG. 1.
Figure 8:
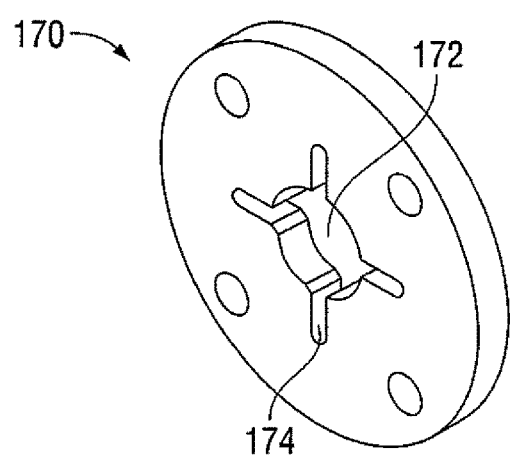
FIG. 8 is a perspective view of the scope retention member of the obturator housing of the optical access apparatus of FIG. 1.

With reference to FIGS. 6B and 6C, the optical member 20 may be is fabricated from a polymeric material, e.g., LEXAN, and is transparent, or at least semi-transparent, to permit passage of light rays. During assembly, the optical member 20 may be over-molded onto the metal obturator shaft 18 to connect the components. In particular, the obturator shaft 18 includes a distal shaft section which depends radially inwardly relative to the longitudinal axis A-A. The optical member 20 is molded to encapsulate the distal shaft section and is secured to the obturator shaft 18 upon curing of the polymeric material. The optical member 20 defines an internal chamfered or sloped surface 201 which is obliquely arranged relative to the longitudinal axis A-A. The chamfered surface 201 is directly engaged by the outermost periphery of the distal end of the endoscope (see FIG. 6C) such that light transmitted from regions of the endoscope radially within the outer periphery travel across an air gap prior to being received by the chamfered or sloped surface 201. The optical member 20 permits the passage of light rays to enable viewing, (by the endoscope) of tissue adjacent the optical member 20 during the insertion and/or advancement of the visual obturator system 10 through the tissue.

The obturator housing 12 of the obturator assembly 11 includes an opening 160 (FIG. 7) and a scope retention member 170 (shown separately in FIG. 8) adjacent the opening 160. The scope retention member 170 is fabricated from an elastomeric material, and defines a central opening 172 for receiving the endoscope and four radial slits 174 extending outwardly from the central opening 172. The radial slits 174 permit flexure of the scope retention member 170 and enlargement of the central opening 172 upon insertion of the endoscope. The scope retention member 170 is adapted to engage the outer surface of the endoscope in frictional engagement therewith to assist in retaining the relative positioning of the endoscope within the obturator assembly 11.

Referring back to FIG. 1, the cannula assembly 100 of the visual obturator system 10 may include a clear elongated portion 102, defining a longitudinal axis "B-B," and a cover 110. The cover 110 encloses an instrument instrument seal 130 and a zero-closure seal 150. The instrument seal 130 is disposed proximally of the zero-closure seal 150.

Figure 9:
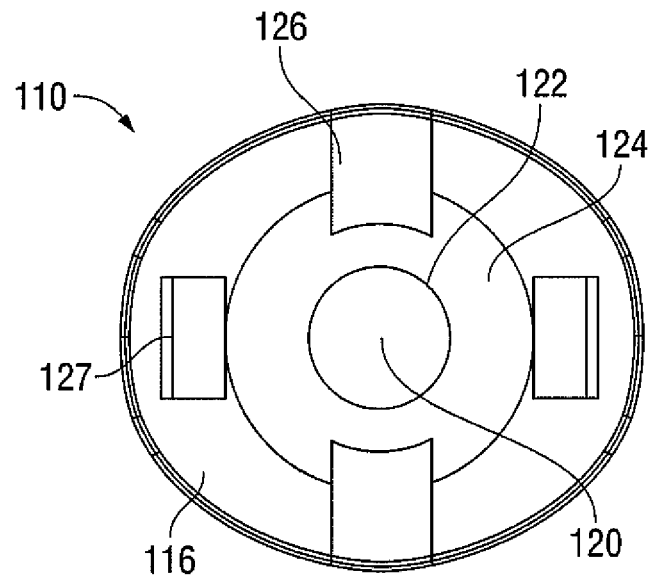
FIG. 9 is a top view of the cover of the cannula assembly of FIG. 2.
Figure 10:
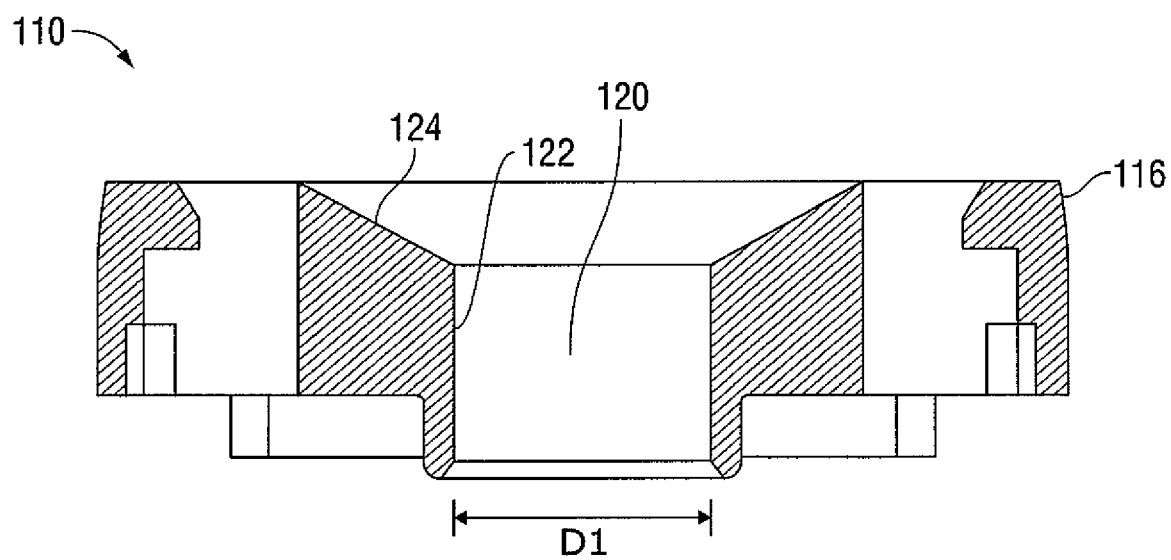
FIG. 10 is a cross sectional view of the cover of the cannula assembly.
Figure 11:
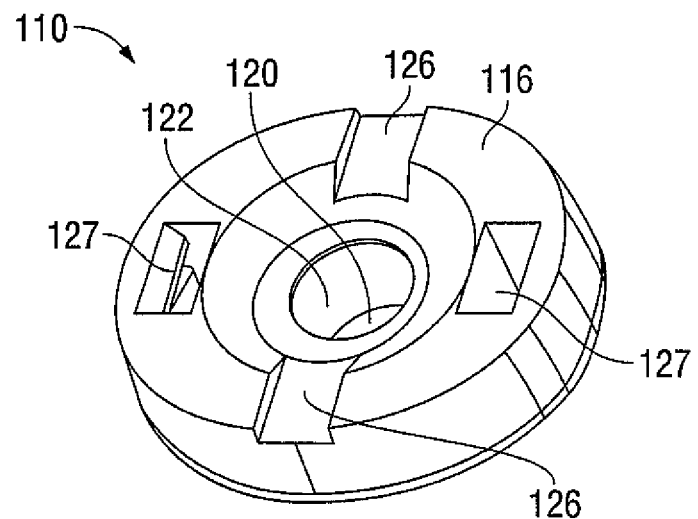
FIG. 11 is a perspective view of the cover of the cannula assembly of FIG. 1.

The cover 110 is configured to mechanically engage a proximal portion of the elongated portion 102 and helps maintain the instrument seal 130 and the zero-closure seal 150 within the cannula housing. Referring to FIG. 9, cover 110 includes an outer periphery 116, and an aperture 120 having a diameter of D1. A ramped section 124 interconnects the outer periphery 116 with the aperture 120. Additionally, the aperture 120 is defined between vertical, inner sidewalls 122 (FIG. 10). Cover 110 also includes a pair of notches 126 and a pair of engagement portions 127 thereon. Notches 126 and engagement portions 127 are configured to be mechanically engaged by a pair of protuberances 23 and a pair of latches 19, respectively, disposed on the obturator member 14 (see FIG. 1). Referring to FIG. 1, buttons 27 on the latches 19 extend through openings 21 in the obturator housing 12, which enables a user to selectively lock and unlock the obturator to and from the cannula assembly 100 (e.g., by pushing the buttons 27 such that the proximal ends of latches 19 engage engaging portions 127 of the cover 110).

Figure 12:
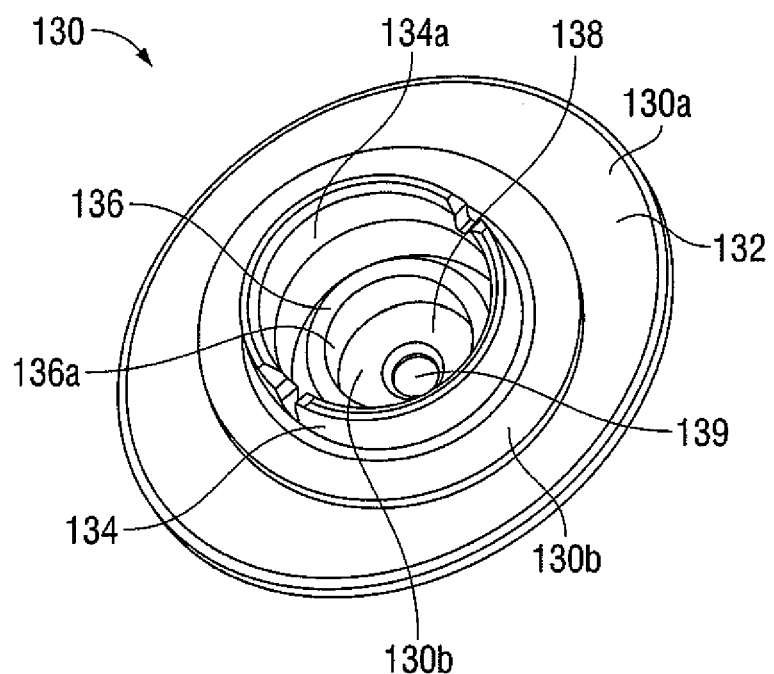
FIG. 12 is a perspective view of the instrument seal of the cannula assembly of FIG. 1.
Figure 13:
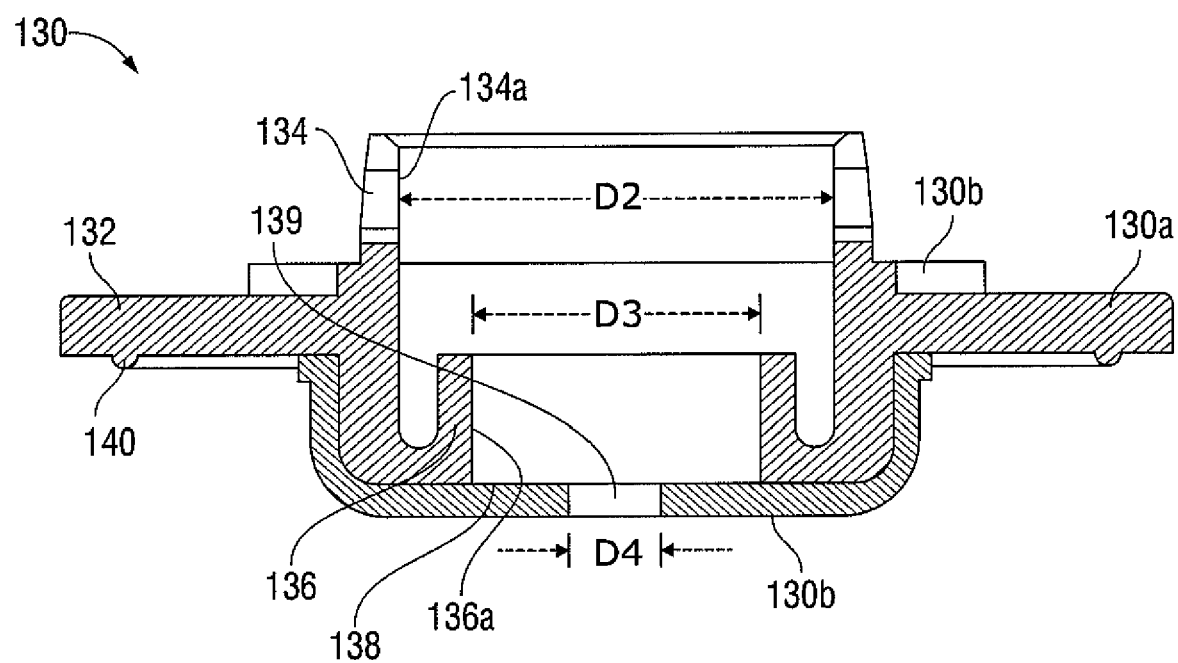
FIG. 13 is a cross-sectional view of the instrument seal of the cannula assembly of FIG. 1.
Figure 14:
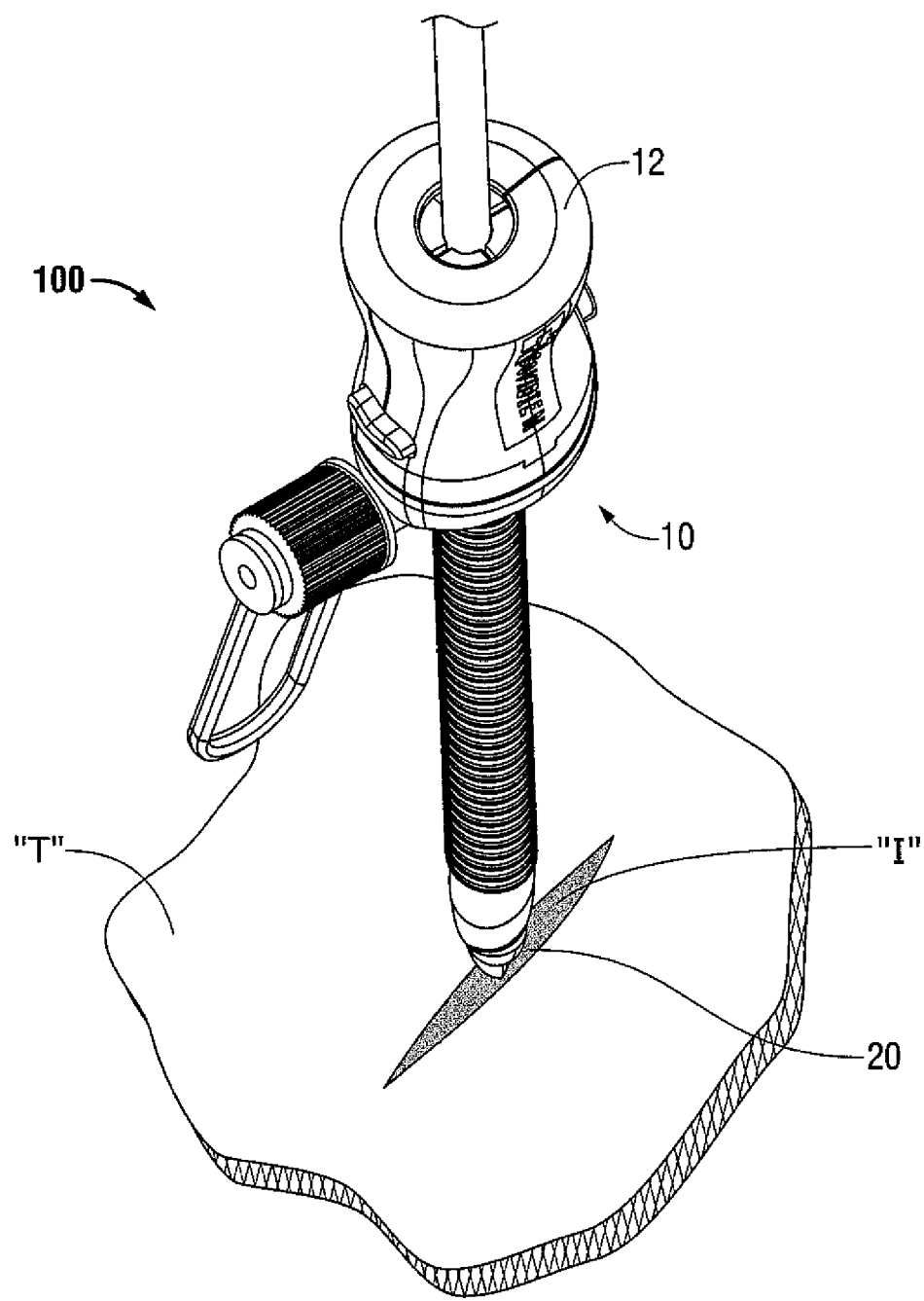
FIG. 14 is a perspective view illustrating an endoscope positioned within the optical access apparatus and accessing body tissue.

Referring now to FIGS. 12 & 13, the instrument seal 130 includes an elastomeric septum seal 130b which is over-molded onto a rigid plastic insert 130a. Rigid plastic insert 130a includes a horizontal surface 132, a first vertical, annular wall 134 and a second vertical, annular wall 136. An inner vertical surface 134a of annular wall 134 defines diameter D2. An inner vertical surface 136a of annular wall 136 defines diameter D3. Additionally, the elastomeric septum seal 130b of the instrument seal 130 defines a horizontal surface 138 disposed within annular wall 136. The elastomeric septum seal 130b includes an aperture 139 having a diameter D4. The diameter D1 of the cover's aperture 120 is less than the diameter D3 of the annular wall 136. Thus, upon insertion, the obturator member 14 is only able to contact the horizontal surface 138 and the walls defining the aperture 139 of the instrument seal 130.

The instrument seal 130 also includes a lip 140 depending downwardly from horizontal surface 132. The lip 140 engages a corresponding detent (not shown) on the housing, such that the instrument seal 130 cannot move rotationally (e.g., about longitudinal axis "B-B") or radially (e.g., transversely with respect to longitudinal axis "B-B"). Additionally, when the cannula assembly 100 is assembled, instrument seal 130 is clamped to a portion of the housing 102, thus preventing axial (e.g., along longitudinal axis "B-B") movement of the instrument seal 130 and further preventing rotational and radial movement of the instrument seal 130.

In use, the obturator assembly 11 of the visual obturator system 10 is at least partially introduced within the cannula assembly 100 with the obturator member 14 extending through the aperture 139 of the instrument seal 130 and through the zero-closure seal 150. An initial incision in a patient is made by, e.g., a scalpel. The assembled visual obturator system 10 is positioned within the initial incision and against the targeted tissue, e.g., the abdominal lining. As discussed above, an endoscope may be inserted through the obturator assembly 11 such that the distal viewing end of the endoscope is positioned against the chamfered surface of the transparent optical member 20. The endoscope may be retained at this relative position within the obturator assembly 11 by the scope retention member 170 When the obturator member 14 passes through the aperture 139 of the instrument seal 130 (either when longitudinal axis "A-A" is substantially aligned with longitudinal axis "B-B" or when longitudinal axis "A-A" is non-aligned (e.g. spaced from and/or angled) with longitudinal axis "B-B"), the only portion of the instrument seal 130 that is capable of movement is the horizontal surface 138 adjacent aperture 139 and disposed radially within the vertical surface 136a of annular wall 136. The other portions of the instrument seal 130 (including the rigid plastic insert 130a and the portions of the elastomeric septum seal 130b disposed outwardly of rigid plastic insert 130a) are not capable of moving with respect to the aperture 139.

As set forth above, the optical member 20 is manipulated relative to the tissue whereby the atraumatic guiding nub 26 engages tissue and, in combination with the concave and/or convex outer surfaces 244, gently dissect or separate the tissue to gain access to an underlying cavity. During insertion, the tissue adjacent the optical member 20 is viewed with the endoscope. The visual obturator may then be removed from the cannula assembly 100. Instruments may be introduced within the cannula assembly 100 to perform a surgical procedure.

The method of forming, e.g., over-molding, the optical member 20 to the distal region 205 of the elongated obturator member 14 will now be discussed. In an example embodiment, the optical member 20 is molded to encapsulate regions of the distal end portion of the elongated obturator member 14. For example, the optical member 20 may be molded to encapsulate both a first or larger diameter section 203 of the elongated obturator member 14 as well as a second or reduced diameter section 201 that is located distally relative to the first or larger diameter section 203. In addition, the optical member 20 may be molded to encapsulate at least one or more voids in the elongated obturator member 14. In embodiments, any suitable material, e.g., preferably transparent but at least semitransparent or translucent so as to enable at least some light transmission therethrough, for forming the optical member 20 as described above may be utilized. In embodiments, the material of the optical member 20, during manufacture, may be in a molten form such that it may flow into the arrangement shown, e.g., into the spaces defined by the first or larger diameter section 203 and the second or reduced diameter section 201 and into the at least one void 207 of the elongated obturator member 14. Advantageously, the optical member 20 may be molded to the distal region of the elongated obturator member 14 such that an outer surface of the optical member 20 has a diameter that is substantially the same as the outer diameter of the elongated obturator member 14. In this manner, the transition between the outer surface of the optical member 20 and the outer surface of the elongated obturator member 14 is smooth. The smoothness of this transition may provide for greater ease of insertion through, e.g., cannula seals.

The one or more void 207 may have any shape, for example, the semi-circular shape shown in FIGS. 6B and 6C. Additionally or alternatively, the void 207 may have a circular or any other suitable shape. Also, the void 207 may be located such that it extends to the distal-most edge of the elongated obturator member 14, e.g., as shown in FIGS. 6B and 6C. Additionally or alternatively, one or more of the voids 207 may be located such that it does not extend to the distalmost edge of the elongated tubular member 14, but rather the void 207 may have a distalmost edge of its own that is proximal relative to the distalmost end of the elongated obturator member 14.

In embodiments, at least a portion of the material of the obturator member 20 is molded so as to extend into the first or larger diameter section 203 of the elongated tubular member 14 proximal to the reduced or second diameter section 201. This may be done using a mold having a shape that forms the shape of the outer surface of the optical member 20 and by using a tooling pin (not shown) that extends through the elongated obturator member 14. A distalmost end portion of the tooling pin has a shape that forms the shape of the hollowed interior of the optical member 20. The tooling pin may also include a second surface, the second surface being proximal relative to the distalmost end portion and being angled so as to form the chamfered or sloped surface 201 of the optical member 20.

In embodiments, the method of manufacturing the overmolded optical member 20, with its regions of different diameter and its one or more void 207, provides improved rotational resistance between the optical member 20 and the elongated obturator member 14. In addition, it assures that a very high force would be required so as to disengage the optical member 20 from the end of the tubular member 14 in both rotational and axial directions. Because material of the optical member 20 is formed so as to be within the first or larger diameter section 203 of the tubular member 14, the force required to be applied by a surgical instrument against the chamfered surface of the optical member 20 in order to push the optical member 20 off of the elongated tubular member 20 is very high. In other embodiments, optical member 20 may be attached to elongated tubular member 14 through any other suitable conventional means, e.g., adhesives, cements, threaded connection, bayonet coupling, snap fit arrangement, etc.

The optical trocar system of the present invention, in accordance with various embodiments thereof, may provide various advantages as compared to conventional trocar systems. For example, conventional trocars may include an obturator having a sharp tip for penetrating the body cavity. In addition to the safety concerns that may exist when using an obturator having a sharp tip (e.g., inadvertent puncture of tissue), such conventional trocars may require complex mechanical arrangements to protect from inadvertent puncture, thereby increasing the number of components in the device, increasing the time required to manufacture and assemble the device, the number of ways that the device may malfunction during use, the cost of the device, etc. For example, one commonly used arrangement in order to prevent inadvertent cutting of tissue by a sharp tip is a retractable protective shield that covers the sharp tip of the obturator when not in use. The obturator trocar system of the present invention, in accordance with various embodiments thereof, may provide for obturators having only rounded and non-bladed surfaces at its distal end such that, even if the distal end of the obturator inadvertent contacts the tissue, the rounded and non-bladed surfaces does not cut, and in fact is incapable of cutting, the tissue. The optical trocar system of the present invention, in accordance with various embodiments thereof, may also provide for an arrangement that has fewer components as compared to conventional trocars, thereby providing the possibility of decreasing the complexity of the device, simplifying its manufacture, reducing its cost and improving its reliability.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. An optical trocar system, comprising:
an elongated obturator member having a first diameter and a distal region, the distal region having a first diameter section having a diameter that is substantially equal to the first diameter of the elongated obturator member and having a second diameter section distal of the first diameter section and having a diameter that is less than the first diameter;
a shoulder joining the first diameter section and the second diameter section; and
an optical member attached to the distal region of the elongated obturator member such that the second diameter section and the shoulder are embedded in the optical member, the optical member including a first cross-section having an oval shape about a longitudinal axis defined by the optical member and approximately at a longitudinal midpoint of the optical member, the first cross-section orthogonal to the longitudinal axis, and a second cross-section having a circular shape about the longitudinal axis, the second cross-section proximal of the first cross-section,
wherein a distal end portion of the elongated obturator member includes at least one semi-circular shaped notch, a portion of the optical member filling at least a portion of the at least one semi-circular shaped notch to increase a frictional force between the optical member and the elongated obturator member, a central section of an outer surface of the optical member including generally convex surfaces and generally concave surfaces that are positioned circumferentially between the generally convex surfaces.

2. The optical trocar system according to claim 1, further comprising a cannula assembly.

3. The optical trocar system according to claim 2, wherein the elongated obturator member is configured for insertion into the cannula assembly.

4. The optical trocar system according to claim 1, wherein the optical member extends distally from the distal end portion of the elongated obturator member.

5. The optical trocar system according to claim 1, wherein the elongated obturator member defines a longitudinal bore.

6. The optical trocar system according to claim 5, wherein the longitudinal bore is configured to receive an endoscope.

7. The optical trocar system according to claim 6, wherein the optical member is at least partially transparent to permit visualization of tissue with the endoscope.

8. The optical trocar system according to claim 7, wherein the optical member defines an internal sloped surface obliquely arranged relative to a longitudinal axis of the optical member and the elongated obturator member.

9. The optical trocar system according to claim 8, wherein the internal sloped surface is configured and dimensioned to be engaged by an outermost periphery of a distal end of the endoscope.

10. The optical trocar system according to claim 8, wherein the internal sloped surface provides an air gap between the distal end of the endoscope and a distal end of the optical member.

11. The optical trocar system according to claim 1, wherein the optical member is configured to dissect between tissue planes without cutting or incising tissue.

12. The optical trocar system according to claim 1, wherein the optical member defines a rounded guiding nub at its distal-most end.

13. The optical trocar system according to claim 1, wherein the generally convex surfaces of the central section of the outer surface of the optical member include a pair of diametrically opposed generally convex surfaces.

14. The optical trocar system according to claim 13, wherein the generally concave surfaces of the central section of the outer surface of the optical member include a pair of diametrically opposed generally concave surfaces that are positioned circumferentially between the pair of diametrically opposed generally convex surfaces.

15. The optical trocar system according to claim 1, wherein the elongated obturator member includes a housing at the proximal region, the housing including an opening and a scope retention member adjacent the opening for receiving and providing retention of an endoscope.

16. The optical trocar system according to claim 1, wherein the optical member is molded to the distal region of the elongated obturator member such that a portion of the optical member fills the at least one semi-circular shaped notch at the distal end portion of the elongated obturator member.

17. The optical trocar system according to claim 1, wherein the optical member is hollow.

18. The optical trocar system according to claim 1, wherein the optical member is attached to the distal region of the elongated obturator member by being molded thereto.

19. An optical trocar system, comprising:
an optical member molded to a distal end of an elongated obturator member, the optical member including a proximal section, a central section, and a guiding nub, the optical member including a first cross-section having an oval shape about a longitudinal axis of the optical member and adjacent a midpoint along a length of the optical member, the first cross-section orthogonal to the longitudinal axis, and a second cross-section having a circular shape about the longitudinal axis and proximal of the first cross-section, wherein the proximal section includes a pair of diametrically opposed convex surfaces, wherein the central section includes a pair of diametrically opposed generally convex surfaces, and wherein the central section of the outer surface of the optical member further includes a pair of diametrically opposed generally concave surfaces that are positioned circumferentially between the pair of diametrically opposed generally convex surfaces.

20. The optical trocar system according to claim 19, wherein the optical member is configured to dissect between tissue planes without cutting or incising tissue.

21. The optical trocar system according to claim 19, wherein the guiding nub of the optical member includes a rounded portion at its distal-most end.

22. The optical trocar system according to claim 19, wherein a portion of the optical member occupies at least one semi-circular shaped notch disposed at a distal end portion of the elongated obturator member thereby providing a friction fit between the optical member and the elongated obturator member.

23. The optical trocar system according to claim 19, wherein the optical member further includes a third cross-section distal of the first cross-section, the third cross-section having a circular shape having a diameter smaller than a diameter of the second cross-section.

* * * * *

UNITED STATES PATENT AND TRADEMARK OFFICE
CERTIFICATE OF CORRECTION

| | |
|---|---|
| PATENT NO. | : 10,813,536 B2 |
| APPLICATION NO. | : 14/351674 |
| DATED | : October 27, 2020 |
| INVENTOR(S) | : Gregory Fischvogt |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 480 days.

Signed and Sealed this
Seventh Day of February, 2023

Katherine Kelly Vidal
*Director of the United States Patent and Trademark Office*